United States Patent
Ohsawa

(10) Patent No.: US 9,662,072 B2
(45) Date of Patent: May 30, 2017

(54) EXERCISE INFORMATION DETECTING APPARATUS, EXERCISE INFORMATION DETECTING METHOD, AND COMPUTER-READABLE STORAGE MEDIUM HAVING EXERCISE INFORMATION DETECTION PROGRAM STORED THEREON

(71) Applicant: CASIO COMPUTER CO., LTD., Shibuya-ku, Tokyo (JP)

(72) Inventor: Toshihiro Ohsawa, Akishima (JP)

(73) Assignee: CASIO COMPUTER CO., LTD., Tokyo (JP)

(*) Notice: Subject to any disclaimer, the term of this patent is extended or adjusted under 35 U.S.C. 154(b) by 703 days.

(21) Appl. No.: 14/032,012

(22) Filed: Sep. 19, 2013

(65) Prior Publication Data
US 2014/0081156 A1   Mar. 20, 2014

(30) Foreign Application Priority Data

Sep. 20, 2012 (JP) ................................ 2012-206545

(51) Int. Cl.
*A61B 5/02* (2006.01)
*A61B 5/00* (2006.01)
(Continued)

(52) U.S. Cl.
CPC ............ *A61B 5/721* (2013.01); *A61B 5/0006* (2013.01); *A61B 5/0205* (2013.01);
(Continued)

(58) Field of Classification Search
CPC ... A61B 5/1123; A61B 5/721; A61B 5/02438; A61B 5/1118; A61B 5/0006;
(Continued)

(56) References Cited

U.S. PATENT DOCUMENTS 5,759,156 A * 6/1998 Hayakawa ......... A61B 5/02438
600/483
6,081,742 A   6/2000 Amano et al.
(Continued)

FOREIGN PATENT DOCUMENTS

CN   1206337 A   1/1999
JP   59-069059 A   4/1984
(Continued)

OTHER PUBLICATIONS

Japanese Office Action Dated Jul. 28, 2014 in counterpart Japanese Application No. 2012-206545.
(Continued)

*Primary Examiner* — Navin Natnithithadha
*Assistant Examiner* — Eric Messersmith
(74) *Attorney, Agent, or Firm* — Holtz, Holtz & Volek PC

(57) ABSTRACT

An exercise information detecting apparatus of the present invention includes a heartbeat sensor which detects heartbeat data of a human body including a waveform signal, an exercise status detecting section which detects exercise data regarding an exercise status of the human body, an exercise status judging section which judges a change of the exercise status of the human body based on the exercise data detected by the exercise status detecting section, and a heart rate calculating section which removes, as a noise component, an invalid peak from among a plurality of peaks included in the waveform signal of the heartbeat data based on the change of the exercise status of the human body judged by the exercise status judging section.

9 Claims, 12 Drawing Sheets

(51) Int. Cl.
*A61B 5/0205* (2006.01)
*A61B 5/11* (2006.01)
*A61B 5/0402* (2006.01)
*A61B 5/04* (2006.01)
*A61B 5/024* (2006.01)
*G01C 22/00* (2006.01)

(52) U.S. Cl.
CPC ........ *A61B 5/02438* (2013.01); *A61B 5/0402* (2013.01); *A61B 5/04012* (2013.01); *A61B 5/1118* (2013.01); *A61B 5/1123* (2013.01); *A61B 5/681* (2013.01); *G01C 22/006* (2013.01); *A61B 5/6823* (2013.01); *A61B 5/6831* (2013.01)

(58) Field of Classification Search
CPC ... A61B 5/681; A61B 5/0402; A61B 5/04012; A61B 5/0205; G01C 22/006
See application file for complete search history.

(56) References Cited

U.S. PATENT DOCUMENTS

| | | | |
|---|---|---|---|
| 7,438,688 B2 | 10/2008 | Kobayashi et al. | |
| 2003/0229289 A1* | 12/2003 | Mohler | A61B 5/04023 600/508 |
| 2009/0082681 A1 | 3/2009 | Yokoyama et al. | |
| 2009/0204011 A1* | 8/2009 | Suzuki | A61B 5/02416 600/500 |
| 2013/0006123 A1* | 1/2013 | Aoshima | A61B 5/02438 600/483 |

FOREIGN PATENT DOCUMENTS

| | | |
|---|---|---|
| JP | 01-126206 U | 8/1989 |
| JP | 05-212136 A | 8/1993 |
| JP | 07-105337 A | 4/1995 |
| JP | 09-113309 A | 5/1997 |
| JP | 09-154825 A | 6/1997 |
| JP | 2002-263086 A | 9/2002 |
| JP | 2004-101346 A | 4/2004 |
| JP | 2005-095653 A | 4/2005 |
| JP | 2007-054471 A | 3/2007 |
| JP | 2009072417 A | 4/2009 |
| JP | 2011-221798 A | 11/2011 |

OTHER PUBLICATIONS

Chinese Office Action dated Feb. 17, 2015, issued in counterpart Chinese Application No. 201310429114.3.

* cited by examiner

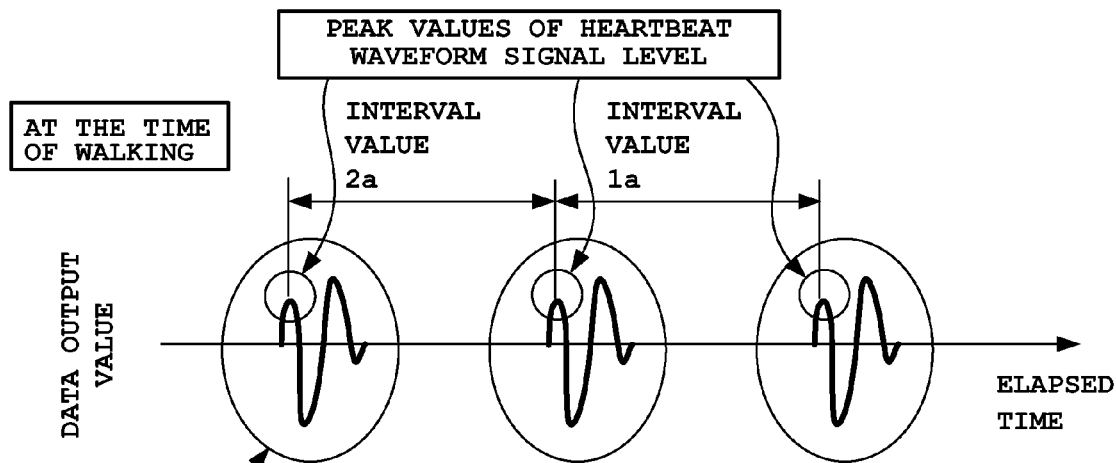
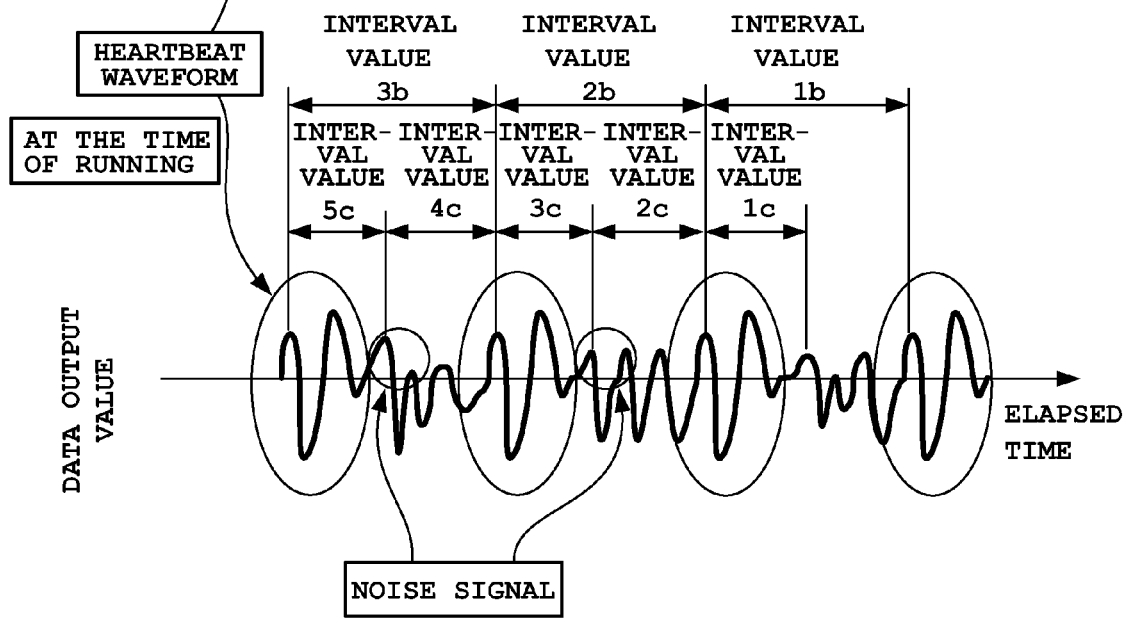

EXERCISE INFORMATION DETECTING APPARATUS, EXERCISE INFORMATION DETECTING METHOD, AND COMPUTER-READABLE STORAGE MEDIUM HAVING EXERCISE INFORMATION DETECTION PROGRAM STORED THEREON

CROSS-REFERENCE TO RELATED APPLICATION

This application is based upon and claims the benefit of priority from the prior Japanese Patent Application No. 2012-206545, filed Sep. 20, 2012, the entire contents of which are incorporated herein by reference.

BACKGROUND OF THE INVENTION

1. Field of the Invention

The present invention relates to an exercise information detecting apparatus, an exercise information detecting method, and a computer-readable storage medium having an exercise information detection program stored thereon. Specifically, the present invention relates to an exercise information detecting apparatus having a heartbeat measurement function for measuring heartbeat data with the apparatus being mounted on a human body at the time of an exercise, an exercise information detecting method, and a computer-readable storage medium having an exercise information detection program stored thereon.

2. Description of the Related Art

In recent years, because of rising health consciousness, more and more people are performing daily exercises, such as running, walking, and cycling, to maintain their wellness or improve their health condition. In addition, an increasing number of people are aiming to participate in a competition (race) such as a marathon race through these daily exercises. These people are highly conscious of and interested in measuring and recording their own health conditions and exercise status by using numerical values or data. Currently, various measuring devices supporting this demand are commercially available. By measuring and recording a footstep count, movement distance, pulsation (heart rate), calorie consumption amount, and the like, their own health conditions and exercise status can be grasped.

As an example of this type of measuring device, a heartbeat measuring apparatus disclosed in Japanese Patent Application Laid-Open (Kokai) Publication No. 05-212136 has been known, which includes a heartbeat detector that is worn on a chest part and a heartbeat display apparatus that is worn on an arm part. In general, as a method for counting a heart rate applied to a heartbeat measuring apparatus, a scheme of measuring time between heartbeat signals is applied. On the other hand, it has been known that, when the heartbeat measuring apparatus is mounted on a human body to measure the heart rate during an exercise such as running or running in a marathon, a contact state between the human body and an electrode of the heartbeat detector may become non-uniform and unstable, whereby noise may be generated, or a signal other than heartbeat generated from the human body by the exercise may occur as noise. As a result, in the above-described method for counting a heart rate, if a noise component generated due to the movement of the human body is erroneously detected as a heartbeat signal, the heart rate may not be able to be measured correctly. As a method to solve this problem, for example, a method is known in which noise components occurred due to the movement of a human body (body motion) are removed from a detected signal by using a filter, as disclosed in Japanese Patent Application Laid-Open (Kokai) Publication No. 2007-054471.

In the above-described noise removal method using a filter, when a measurement subject (user) wearing a heartbeat measuring apparatus stays still, noise is favorably removed. Therefore, this method is quite effective. However, with this method, in some cases, it is not possible to sufficiently remove only noise components from noise occurred at the time of an exercise. As a result, the number of times a non-removed noise component is erroneously detected as a heartbeat signal is increased, and a heart rate higher than the true value is disadvantageously calculated.

The present invention has been conceived in light of the above-described problems. An object of the present invention is to provide an exercise information detecting apparatus, an exercise information detecting method, and a non-transitory computer-readable storage medium having an exercise information detection program stored thereon by which an accurate heart rate is measured even when a measurement subject is performing an exercise.

SUMMARY OF THE INVENTION

In accordance with one aspect of the present invention, there is provided an exercise information detecting apparatus comprising: a heartbeat sensor which detects heartbeat data of a human body including a waveform signal; an exercise status detecting section which detects exercise data regarding an exercise status of the human body; an exercise status judging section which judges a change of the exercise status of the human body based on the exercise data detected by the exercise status detecting section; and a heart rate calculating section which removes, as a noise component, an invalid peak from among a plurality of peaks included in the waveform signal of the heartbeat data based on the change of the exercise status of the human body judged by the exercise status judging section.

In accordance with another aspect of the present invention, there is provided an exercise information detecting method comprising: a step of detecting heartbeat data of a human body including a waveform signal by a heartbeat sensor; a step of detecting exercise data including a waveform signal related to an exercise status of the human body by an exercise status detecting section; a step of judging a change of the exercise status of the human body based on clock data between peak values of a signal level of the waveform signal included in the exercise data; and a step of removing, as a noise component, an invalid peak from among a plurality of peaks included in the waveform signal of the heartbeat data, based on the judged change of the exercise status of the human body.

In accordance with another aspect of the present invention, there is provided a non-transitory computer-readable storage medium having stored thereon an exercise information detection program that is executable by a computer, the program being executable by the computer to perform functions comprising: processing for detecting heartbeat data of a human body including a waveform signal by a heartbeat sensor; processing for detecting exercise data including a waveform signal related to an exercise status of the human body by an exercise status detecting section; processing for judging a change of the exercise status of the human body based on clock data between peak values of a signal level of the waveform signal included in the exercise data; and processing for removing, as a noise component, an invalid peak from among a plurality of peaks included in the waveform signal of the heartbeat data, based on the judged change of the exercise status of the human body.

According to the present invention, an accurate heart rate can be measured even when a measurement subject is performing an exercise.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 9A and FIG. 9B are signal waveform diagrams depicting examples of heartbeat data at the time of walking and running outputted from a heartbeat sensor applied in the exercise support apparatus according to the first embodiment;

DETAILED DESCRIPTION OF THE PREFERRED EMBODIMENTS

<First Embodiment>
(Exercise Support Apparatus)
First, an exercise support apparatus in which an exercise information detecting apparatus according to the present invention has been applied is described.

Figure 1A:
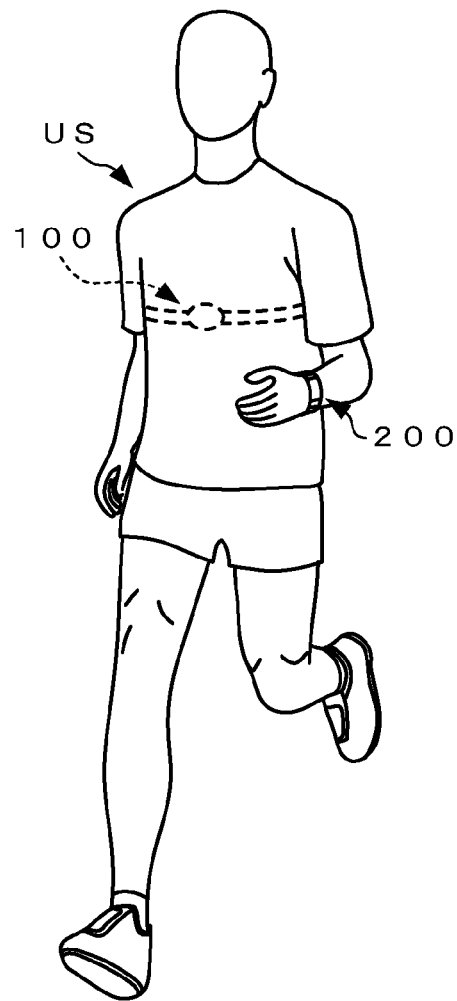
FIG. 1A to FIG. 1C are schematic structural diagrams depicting a first embodiment of an exercise support apparatus in which an exercise information detecting apparatus according to the present invention has been applied.
Figure 1C:
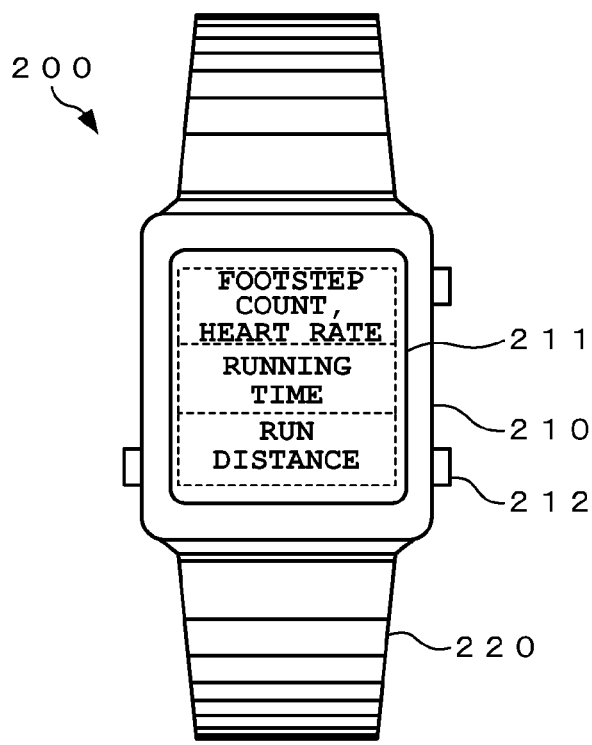
Figure 1B:
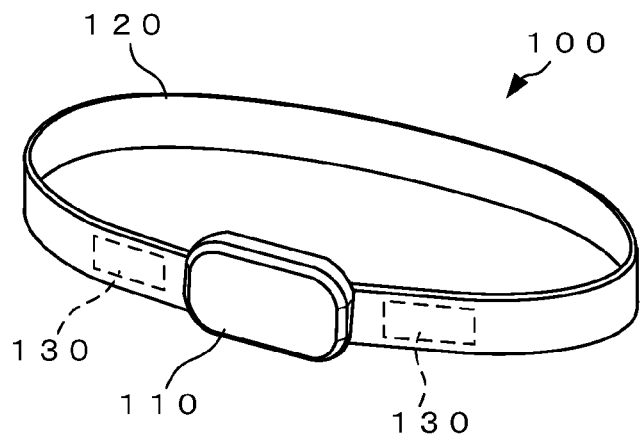

FIG. 1A to FIG. 1C are schematic structural diagrams depicting a first embodiment of an exercise support apparatus in which an exercise information detecting apparatus according to the present invention has been applied. Here, FIG. 1A is a schematic view of a state where the exercise support apparatus according to the present embodiment has been worn on a human body, and FIG. 1B is a schematic structural diagram of a sensor device applied in the exercise support apparatus according to the present embodiment. FIG. 1C is a schematic structural diagram of an interface device applied in the exercise support apparatus according to the present embodiment.

The exercise support apparatus in which the exercise information detecting apparatus according to the present invention has been applied mainly includes a sensor device 100 that is worn on the chest part of a user US who is a measurement subject and an interface device 200 that is worn on the wrist, as depicted in FIG. 1A. The sensor device 100 detects various information (hereinafter referred to as "exercise information") regarding an exercise status (for example, a walking status and running status, a footstep count per unit time) when the user US is exercising (for example, walking or running), and calculates the footstep count and the heart rate of the user US. The sensor device 100 mainly includes a device body 110 having a sensor section, a belt section 120 for mounting the device body 110 on the chest part of the user US by being wound around the chest part, and paired detection electrodes 130 provided on the inner surface side of the belt section 120 (the side that comes in contact with the human body), as depicted in FIG. 1B.

The interface device 200 visually provides exercise information including a footstep count and a heart rate calculated by the sensor device 100 and an advice (hereinafter referred to as "support information") regarding the exercise status of the user US analyzed based on the exercise information to the user US. The interface device 200 mainly includes a device body 210 including a display section 211 for providing predetermined information to the user and a belt section 220 for mounting the device body 110 on the wrist of the user US by being wound around the wrist, as depicted in FIG. 1C.

Each component of the exercise support apparatus is specifically described below.

Figure 2:
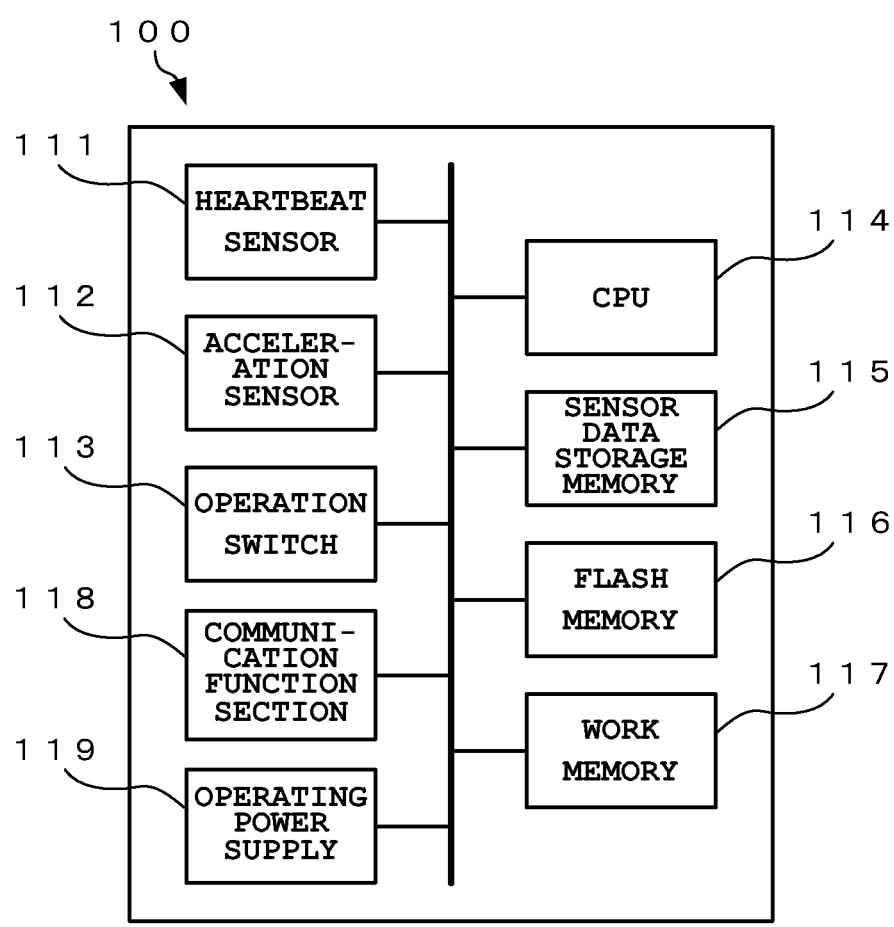
FIG. 2 is a block diagram showing an example of the structure of a sensor device applied in the exercise support apparatus according to the first embodiment.
Figure 3:
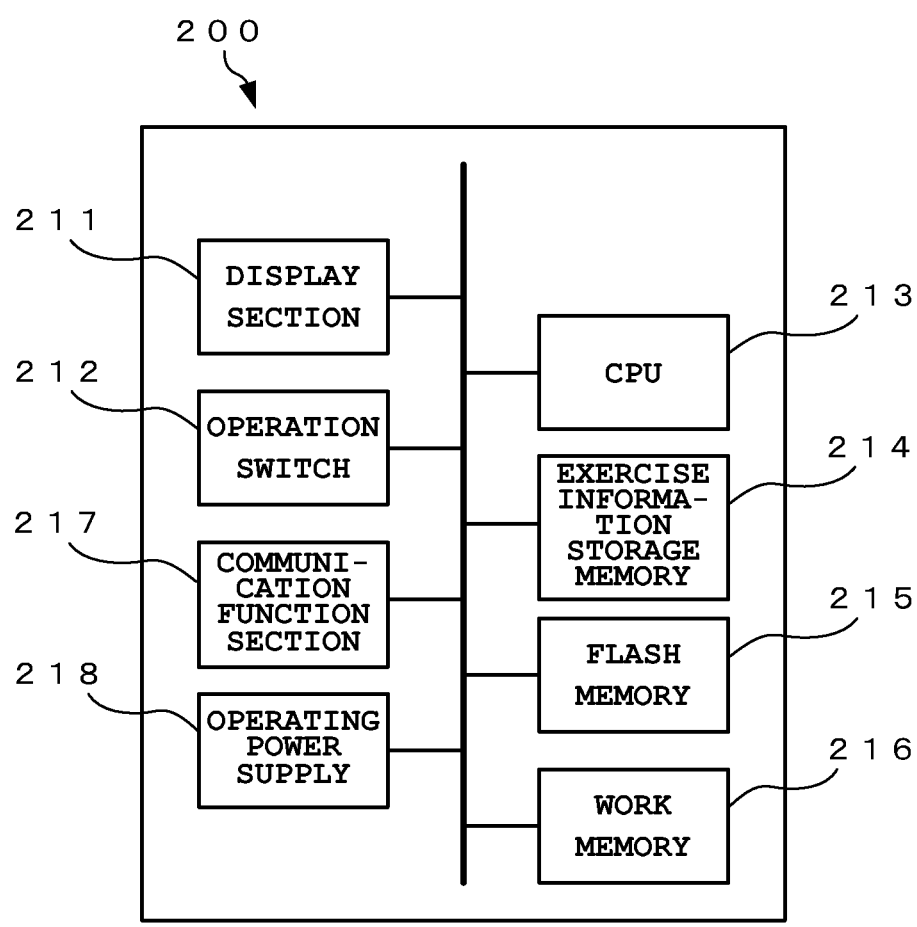
FIG. 3 is a block diagram showing an example of the structure of an interface device applied in the exercise support apparatus according to the first embodiment.

FIG. 2 is a block diagram showing an example of the structure of a sensor device applied in the exercise support apparatus according to the present embodiment, and FIG. 3 is a block diagram showing an example of the structure of an interface device applied in the exercise support apparatus according to the present embodiment.

(Sensor Device 100)

The sensor device 100 specifically includes a heartbeat sensor 111, an acceleration sensor 112, an operation switch 113, a Central Processing Unit (hereinafter referred to as "CPU") 114, a sensor data storage memory 115, a flash memory 116, an work memory 117, a communication function section 118, and an operating power supply 119, as depicted in FIG. 2.

The heartbeat sensor 111 is provided on the inner surface side of the belt section 120 for mounting the sensor device 100 on the chest part of the user US, and has the paired detection electrodes 130 placed so as to directly come in close contact with the chest part of the user US, as depicted in FIG. 1B. The heartbeat sensor 111 detects a change in an electrocardiographic signal outputted from the detection electrodes 130 and outputs heartbeat data (sensor data). This heartbeat data is stored in a predetermined storage area of the sensor data storage memory 115.

The acceleration sensor 112 is provided inside the device body 110, detects a ratio (acceleration) of the change of the motion speed when the user US is exercising, and outputs acceleration data (sensor data; exercise data). The acceleration data is associated with heartbeat data and stored in a predetermined storage area of the sensor data storage memory 115.

The operation switch 113 has a power supply switch and, by the user US operating this operation switch 113, the state of supplying (or cutting) driving electric power from the operating power supply 119 to each structure is controlled to control ON and OFF of the power supply of the sensor device 100. Also, the operation switch 113 has a sensor control key switch and, by the user US operating the operation switch 113, the start or stop of a sensing operation in the heartbeat sensor 111 and the acceleration sensor 112 is controlled.

The sensor data storage memory 115 stores, in a predetermined storage area, heartbeat data outputted from the heartbeat sensor 111 and acceleration data obtained through measurement by the acceleration sensor 112 in association with each other. The flash memory 116 has stored therein a control program for performing a predetermined operation in each component, such as a sensing operation in the heartbeat sensor 111 and the acceleration sensor 112 and a data transmitting operation in the communication function section 118 which will be described below, and an algorithm program for processing sensor data, outputting the footstep count and the heart rate of the user US, and judging the exercise status of the user US. The work memory 117 temporarily stores various data that are used or generated when the control program and the algorithm program are executed. The sensor data storage memory 115 may be partially or entirely a removable storage medium such as a memory card so as to be removable from the sensor device 100.

The CPU 114 performs processing by following the control program stored in the flash memory 116, and thereby controls an operation in each structure, such as a sensing operation in the heartbeat sensor 111 and the acceleration sensor 112 and a data transmitting operation in the communication function section 118. The CPU 114 also performs processing by following the algorithm program, and thereby processes, inside the CPU 114, sensor data obtained by the heartbeat sensor 111 and the acceleration sensor 112 and performs an operation of calculating a footstep count and a heart rate and an operation of judging an exercise status. The control program and the algorithm program to be executed in the CPU 114 may be incorporated inside the CPU 114 in advance.

The communication function section 118 functions as an interface when transmitting, to the interface device 200, exercise information including the footstep count and heart rate of the user US obtained and outputted by processing sensor data obtained by the heartbeat sensor 111 and the acceleration sensor 112 by following the algorithm program. Here, as a method for transmitting exercise information to the interface device 200 via the communication function section 118, for example, various wireless communication methods and wired communication methods via a communication cable can be applied.

In the transmission of the above-described data via a wireless communication method. Bluetooth (registered trademark), which is a short-range wireless communication standard for digital devices, or Bluetooth (registered trademark) low energy (LE) planned as a low-power-consumption type in the above-described communication standard can be favorably applied. By this wireless communication method, data transmission can be favorably performed even with small power generated by, for example, energy harvest technology described below.

The operating power supply 119 supplies driving electric power to each component inside the device body 110 of the sensor device 100. As the operating power supply 119, for example, a primary battery such as a commercially-available coin-shaped battery or button-shaped battery or a secondary battery such as a lithium-ion battery or a nickel metal hydride battery can be applied. In addition, it is possible to apply a power supply by energy harvest technology for generating electricity by energy such as vibrations, light, heat, and electro-magnetic waves.

(Interface Device 200)

The interface device 200 mainly includes the display section 211, an operation switch 212, a Central Processing Unit (hereinafter abbreviated as "CPU") 213, an exercise information storage memory 214, a flash memory 215, a work memory 216, a communication function section 217, and an operating power supply 218, as depicted in FIG. 3.

The display section 211 has, for example, a display device such as a liquid-crystal display panel capable of color or monochrome display or an organic EL display panel, and displays at least various exercise information calculated based on sensor data detected by the sensor device 100 when the user US is exercising. On the display section 211, in addition to a footstep count and a heart rate, numerical value information such as a running time, a running speed (pace), and a run distance is displayed in an arbitrary layout, as depicted in FIG. 1C. These pieces of information may be simultaneously displayed on the display section 211, or may be sequentially displayed or singly displayed by operating the operation switch 212 described above or a touch panel. Also, the display section 211 may display predetermined support information according to the exercise status of the user US judged by an exercise support method described below so as to visually provide the support information to the user US. In the present embodiment, the display section 211 is described as an output interface in the interface device 200. However, the present invention is not limited thereto. In addition to the display section 211, another interface may be provided such as an acoustic section such as a buzzer or loudspeaker which emits, for example, a specific timbre or a voice message, or a vibrating section which vibrates with a specific vibration pattern.

The operation switch 212 has a button switch as depicted in FIG. 1C, which is used for setting various items to be displayed on the display section 211 and performing an operation of inputting various set values associated with other operations of the interface device 200. In the present embodiment, the operation switch 212 having a button switch is described as an input interface in the interface device 200. However, the present invention is not limited thereto. In addition to or in place of the operation switch 212, another interface may be provided such as a touch panel provided on the view field side of the display section 211.

The exercise information storage memory 214 stores, in a predetermined storage area, exercise information including the footstep count and the heart rate of the user US transmitted from the sensor device 100 in association with each other. The flash memory 215 stores a control program for performing a predetermined operation in each component such as an operation of displaying exercise information and support information on the display section 211 and an operation of transmitting data in the communication function section 217, which will be described below. The work memory 216 temporarily stores various data that are used or generated when the control program is performed. The exercise information storage memory 214 may be partially or entirely a removable storage medium such as a memory card so as to be removable from the interface device 200.

The CPU 213 performs processing by following the control program stored in the flash memory 215, and thereby controls an operation in each component such as an operation of displaying exercise information and support information on the display section 211 and an operation of transmitting data in the communication function section 217. The control program which is executed in the CPU 213 may be incorporated in advance inside the CPU 213.

The communication function section 217 functions as an interface with the sensor device 100 when transmitting exercise information including at least the footstep count and the heart rate of the user US by using a predetermined wireless or wired communication method.

The operating power supply 218 supplies driving electric power to each component inside the device body 210 of the interface device 200. As the operating power supply 218, a primary battery such as a commercially-available coin-shaped battery, a secondary battery such as a lithium-ion battery, a power supply by energy harvest technology, etc. can be applied, as in the case of the sensor device 100 described above.

(Exercise Support Method)

Next, the exercise support method for the above-described exercise support apparatus is described. Here, in the exercise support method according to the present embodiment, an exercise information detecting method according to the present invention is applied.

Figure 4:
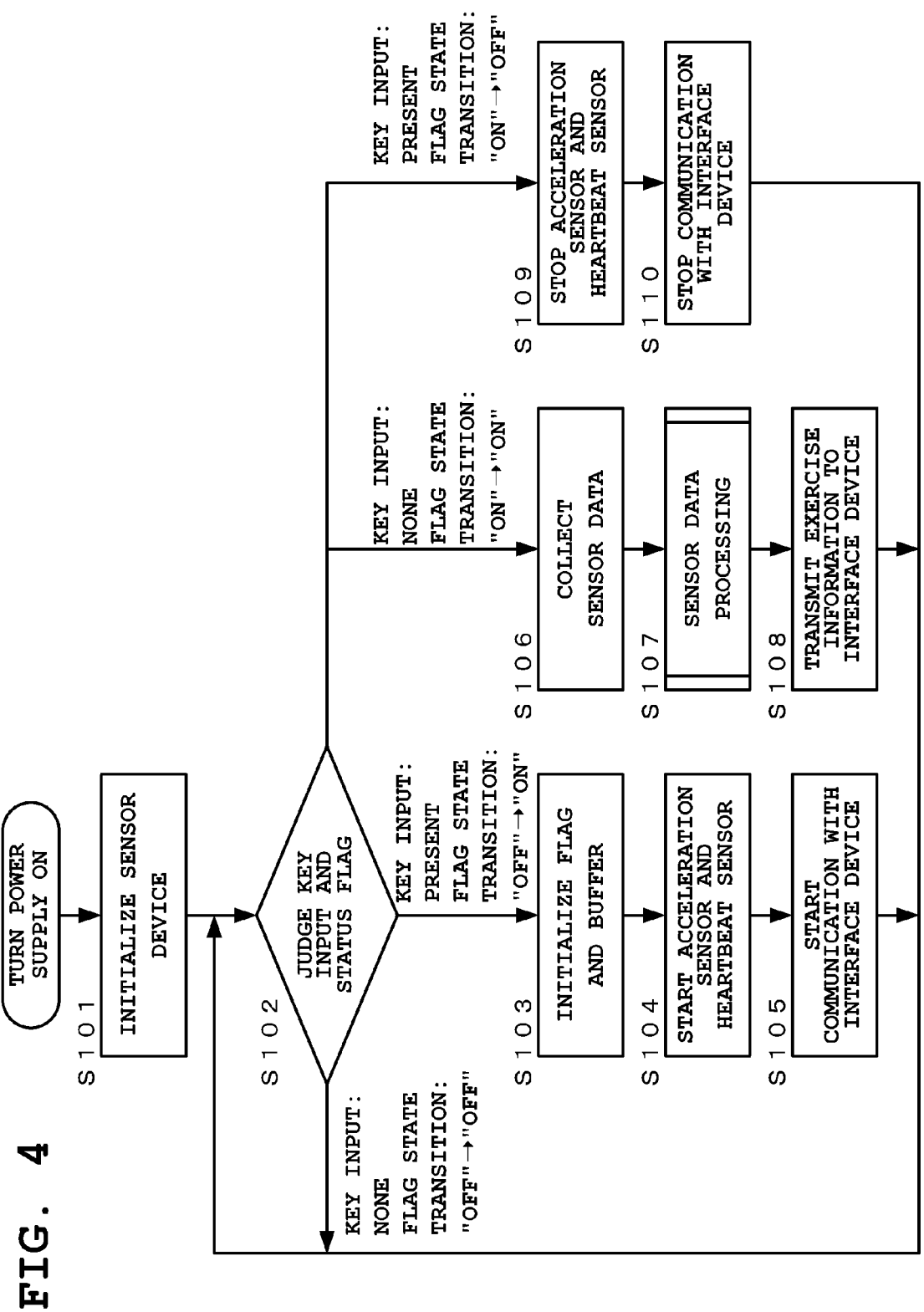
FIG. 4 is a flowchart of an exercise information detecting method that is executed by the sensor device applied in the exercise support apparatus according to the first embodiment.

FIG. 4 is a flowchart of the exercise information detecting method that is executed by the sensor device applied in the exercise support apparatus according to the present embodiment.

The exercise support method in the above-structured exercise support apparatus is performed with a series of procedures mainly including a sensing operation in the sensor device 100, an operation of processing sensor data, an operation of transmitting exercise information to the interface device 200, and an operation of providing exercise information and support information to the user US.

First, the sensing operation in the sensor device 100, the sensor data processing operation, and the operation of transmitting exercise information to the interface device 200 are described.

In the above-described sensor device 100, by operating the operation switch (power supply switch) 113, the power supply is set to an ON state, whereby the CPU 114 starts various processing. Then, at Step S101, the CPU 114 first performs initial setting of each component (hardware) of the sensor device 100 and each program (software), as depicted in the flowchart of FIG. 4.

Next, at Step S102, the CPU 114 judges the operation status (the presence or absence of a key input) of the operation switch (sensor control key switch) and a key status flag set based on the operation of the operation switch, and classifies the current state into four states, as depicted in Table 1. Then, the CPU 114 performs the following processing according to a state obtained by the classification. Note that the processing for judging the operation status (key input) of the operation switch and the key status flag at Step S102 is repeatedly performed at, for example, predetermined time intervals. Also, the operation switch may be provided to the sensor device 100 or may be provided to the interface device 200.

TABLE 1

<PROCESSING FOR JUDGING KEY INPUT AND STATUS FLAG>

| KEY INPUT | FLAG | STATE TRANSITION | PROCESSING TO BE PERFORMED |
|---|---|---|---|
| PRESENT | OFF | KEY: START/FLAG: OFF→ON | STEP S103 |
| NONE | ON | KEY: —/FLAG: ON→ON | STEP S106 |
| PRESENT | ON | KEY: STOP/FLAG: ON→OFF | STEP S109 |
| NONE | OFF | KEY: —/FLAG: OFF→OFF | STEP S102 |

That is, at Step S102, if a key input [present] is detected when the key status flag is "OFF" as depicted in Table 1, the CPU 114 causes the heartbeat sensor 111 and the acceleration sensor 112 to perform a sensing operation, and also changes and sets the key status flag from "OFF" to "ON". Then, the CPU 114 performs sensor start processing in the following Steps S103 to S105.

In the sensor start processing, at Step S103, the CPU 114 first sets a flag and a buffer to a default value for initialization, as depicted in management information of Table 2. Next, at Step S104, the CPU 114 starts the heartbeat sensor 111 and the acceleration sensor 112 to start collection of sensor data (sensing operation). Also, at Step S105, the CPU 114 starts the communication function section 118 to start an operation of transmitting exercise information including a heart rate and a footstep count calculated based on the sensor data to the interface device 200. Then, when the sensor start processing including these Steps S103 to S105 ends, the CPU 114 returns to Step S102, where the processing for judging a key input and a status flag is performed again.

TABLE 2

<MANAGEMENT INFORMATION>

|  | DEFAULT VALUE | OTHER CHANGED VALUE |
|---|---|---|
| FOOTSTEP COUNT INFORMATION | 0 |  |
| HEART RATE INFORMATION | 75 |  |
| CLOCK INFORMATION [10] | 0 |  |
| EXERCISE STATUS JUDGMENT INFORMATION | STOP | WALKING UP |
| PREVIOUS INTERVAL VALUE INFORMATION [10] | 0 |  |
| ALLOWABLE RANGE LOWER-LIMIT VALUE | 0.8 | 0.7 |
| ALLOWABLE RANGE UPPER-LIMIT VALUE | 1.2 | 1.3 |

Then, at Step S102, if no key input is detected (that is, if a key input [none] is detected) when the key status flag is "OFF" as depicted in Table 1, the CPU 114 maintains the current operation status of the sensor device 100 and the "OFF" state of the key status flag. Then, the CPU 114 returns to Step S102, where the judgment processing described above is performed again.

At Step S102, if the CPU 114 detects no key input (that is, a key input [none]) when the key status flag is "ON" as depicted in Table1, the CPU 114 maintains the current operation status of the sensor device 100 and the "ON" state of the key status flag. Then, the CPU 114 performs data collection and data processing in the following Steps S106 to S108.

In the data collection and the data processing, at Step S106, the CPU 114 first causes the heartbeat sensor 111 and the acceleration sensor 112 to regularly collect sensor data (heartbeat data and acceleration data). For example, the CPU 114 causes the heartbeat sensor 111 to collect heartbeat data at an interval of 200 Hz and causes the acceleration sensor 112 to collect acceleration data at an interval of 100 Hz. Next, at Step S107, the CPU 114 processes the collected sensor data. Here, the CPU 114 processes the heartbeat data as a "heart rate", and processes the acceleration data as a "footstep count" at the time of walking or running. A specific example of the sensor data processing will be described further below. Next, at Step S108, the CPU 114 regularly transmits the "heart rate" and the "footstep count" generated by the above-described processing and various information related to the exercise status of the user US to the interface device 200, as exercise information. For example, the CPU 114 transmits the exercise information to the interface device 200 at is intervals. Then, when the data collection and the data processing including these Steps S106 to S108 end, the CPU 114 returns to Step S102, where the above-described judgment processing is performed again.

At Step S102, if a key input [present] is detected when the key status flag is "ON" as depicted in Table 1, the CPU 114 ends the sensing operation in the sensor device 100, and changes and sets the key status flag from "ON" to "OFF". Then, the CPU 114 performs sensor stop processing in the following Steps S109 to S110.

In the sensor stop processing, at Step S109, the CPU 114 stops the heartbeat sensor 111 and the acceleration sensor 112 to end the sensing operation. Also, at Step S110, the CPU 114 stops the communication function section 118 to end the transmission of the exercise information to the interface device 200.

(Sensor Data Processing)

Specific examples of footstep count calculation processing and heart rate calculation processing that are performed in the sensor data processing described in the exercise support method are described.

Figure 5:
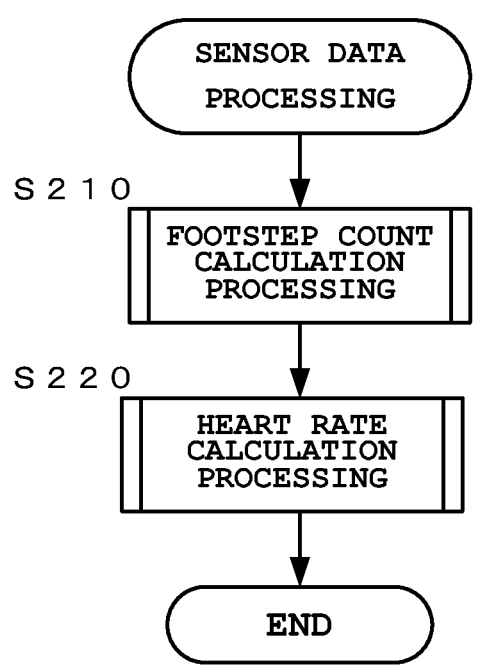
FIG. 5 is a flowchart of a schematic operation of sensor data processing applied in an exercise support method according to the first embodiment.

FIG. 5 is a flowchart of a schematic operation of the sensor data processing applied in the exercise support method according to the present embodiment.

The sensor data processing (Step S107) applied in the exercise support method according to the present embodiment includes footstep count calculation processing (Step S210) and heart rate calculation processing (Step S220), as depicted in FIG. 5. These processing operations are started by the CPU 114 calling each module of the footstep count calculation processing and the heart rate calculation processing of the algorithm program.

In the footstep count calculation processing (Step S210), the CPU 114 executes a footstep count algorithm to perform calculation of a "footstep count" and time measurement between peak values of a signal level of a walking waveform signal from the acceleration data collected at Step S106. Here, the calculated "footstep count" is set in the "footstep count information" depicted in the management information of Table 2. The measurement time (clock data) between peak values of the signal level is set in the "clock information" depicted in the management information of Table 2. In the "clock information", for example, clock data for the last ten seconds is stored.

In the heart rate calculation processing (Step S220), the CPU 114 executes the heart rate algorithm to calculate a "heart rate" from a waveform signal that is the heartbeat data collected at Step S106. Here, the calculated "heart rate" is set in the "heart rate information" depicted in the management information of Table 2.

(Specific Example of Footstep Count Calculation Processing)

First, the footstep count calculation processing applied in the exercise support method according to the present embodiment is described.

Figure 6:
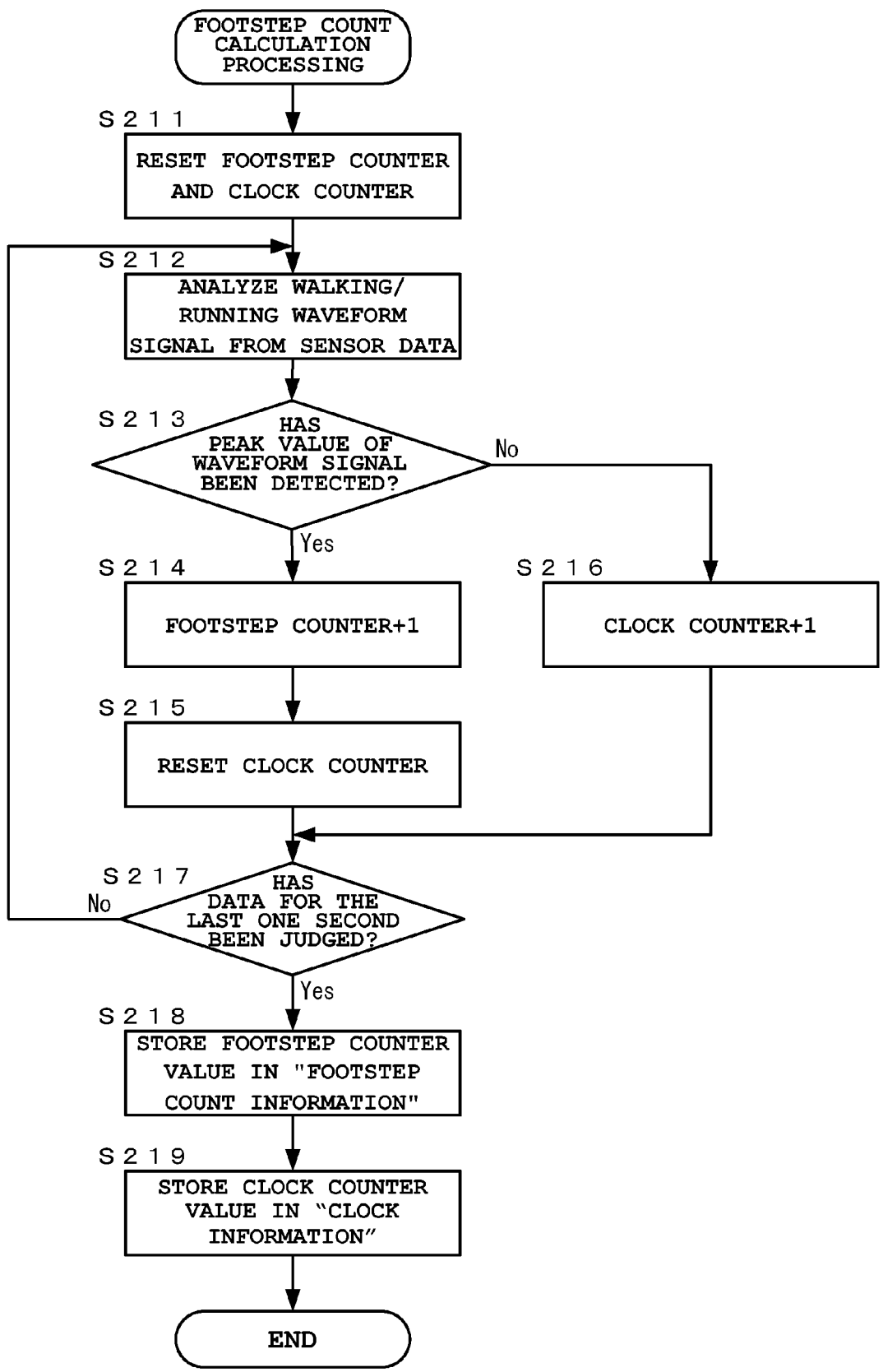
FIG. 6 is a flowchart of footstep count calculation processing applied in the exercise support method according to the first embodiment.
Figures 7A, 7B:
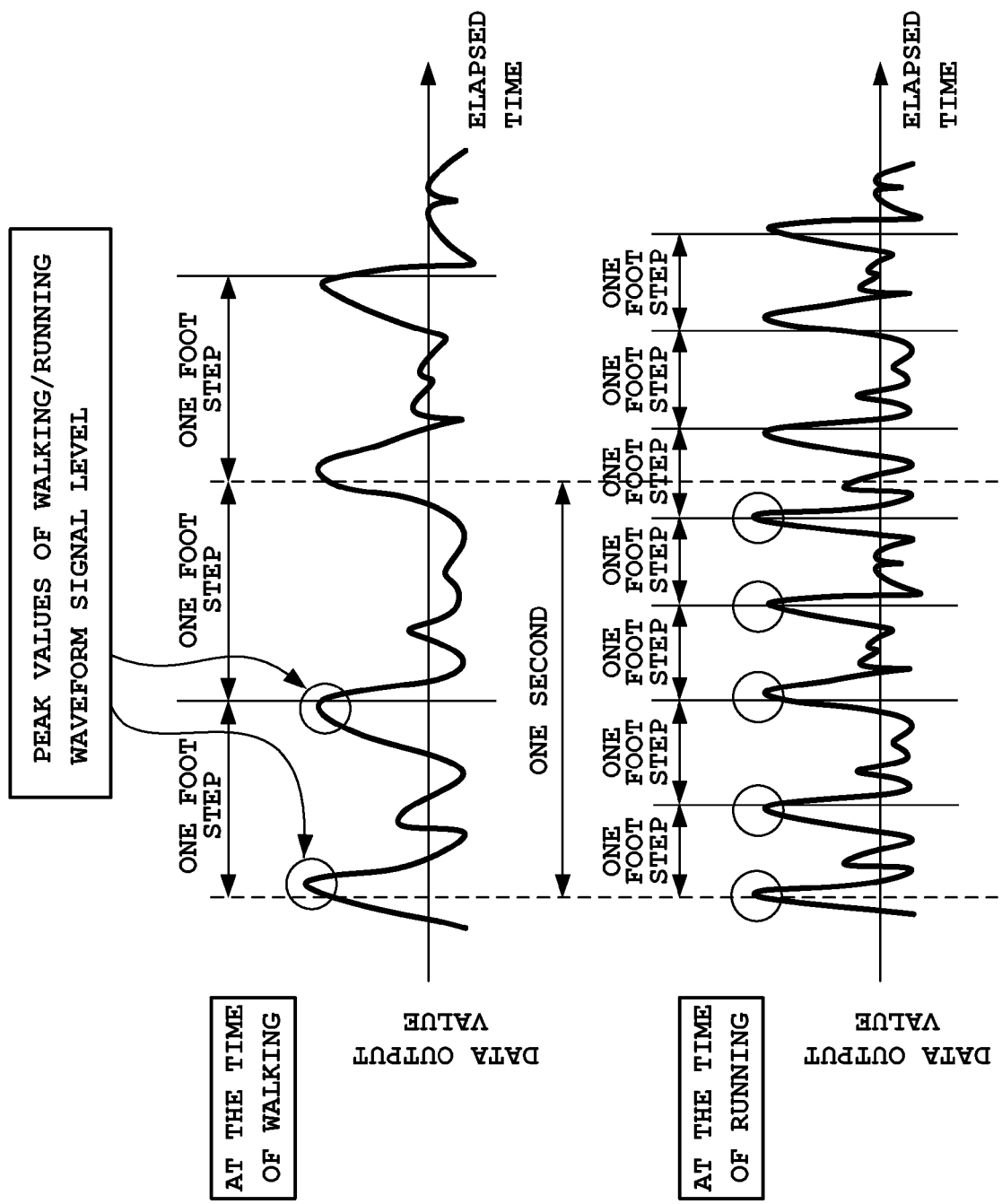
FIG. 7A and FIG. 7B are signal waveform diagrams depicting examples of acceleration data at the time of walking and running outputted from an acceleration sensor applied in the exercise support apparatus according to the first embodiment.

FIG. 6 is a flowchart of the footstep count calculation processing applied in the exercise support method according to the present embodiment. FIG. 7A and FIG. 7B are signal waveform diagrams depicting examples of acceleration data at the time of walking and running outputted from the acceleration sensor applied in the exercise support apparatus according to the present embodiment.

Specifically, in the footstep count calculation processing applied in the present embodiment, at Step S211, the CPU 114 first resets the "footstep counter" for calculating a footstep count for use in the series of footstep count calculation processing and the "clock counter" for measuring a time between peak values of the signal level of the footstep count waveform signal, as depicted in FIG. 6. Next, at Step S212, the CPU 114 starts an operation of sequentially analyzing walking/running waveform signals from output values of the acceleration data detected by the acceleration sensor 112, as depicted in FIG. 7A and FIG. 7B. Then, at Step S213, the CPU 114 judges whether the waveform signal indicates a peak value. When the waveform signal indicates a peak value, the CPU 114 increments the "footstep counter" by 1 (+1) at Step S214. Next, the CPU 114 resets the "clock counter" at Step S215.

On the other hand, when the waveform signal does not indicate a peak value at Step S213, the CPU 114 increments the "clock counter" by 1 (+1) at Step S216, and then proceeds to Step S217. Note that the peak value of the waveform signal herein corresponds to a peak value (a maximum value) of a signal level in a waveform signal indicating acceleration data at the time of each of walking (FIG. 7A) and running (FIG. 7B) outputted from the acceleration sensor 112, as waveform signal portions each surrounded by a circle depicted in FIG. 7A and FIG. 7B.

Next, at Step S217, the CPU 114 judges whether peak value detection processing including Steps S212 to S216 described above has been performed for the output values of the acceleration data for past one second. When judged that the peak value detection processing has not been completed for the output data for the last one second, the CPU 114 returns to Step S212, in which the peak value detection processing including Steps S212 to S216 described above is performed again.

On the other hand, when judged at Step S217 that the peak value detection processing has been completed for the output value for the last one second, the CPU 114 stores at Step S218 the "footstep counter" value in the "footstep count information" depicted in the management information of Table 2. Next, at Step S219, the CPU 114 divides the "clock counter" value by the "footstep counter" value to calculate an average clock counter value per footstep, stores the resultant average value as clock data in the "clock information" depicted in the management information of Table 2, and ends the footstep count calculation processing.

Specifically, in the signal waveforms of the output values of the acceleration data depicted in FIG. 7A and FIG. 7B, as a "footstep counter" value, a counter value of "2" (that is, peak values appear in two footsteps for one second) is set in "footstep count information" at the time of walking, and a counter value of "5" (that is, peak values appear in five footsteps for one second) is set therein at the time of running. Also, as an average clock counter value per footstep, a counter value of "500 ms" (=one second/two footsteps) is set in the "clock information" at the time of walking, and a counter value of "200 ms" (=one second/five footsteps) is set therein at the time of running. Here, as the "clock information" depicted in the management information of Table 2, clock data for the last ten seconds is stored.

(Specific Example of Heart Rate Calculation Processing)

Next, the heart rate calculation processing applied in the exercise support method according to the present embodiment is described.

Figure 8:
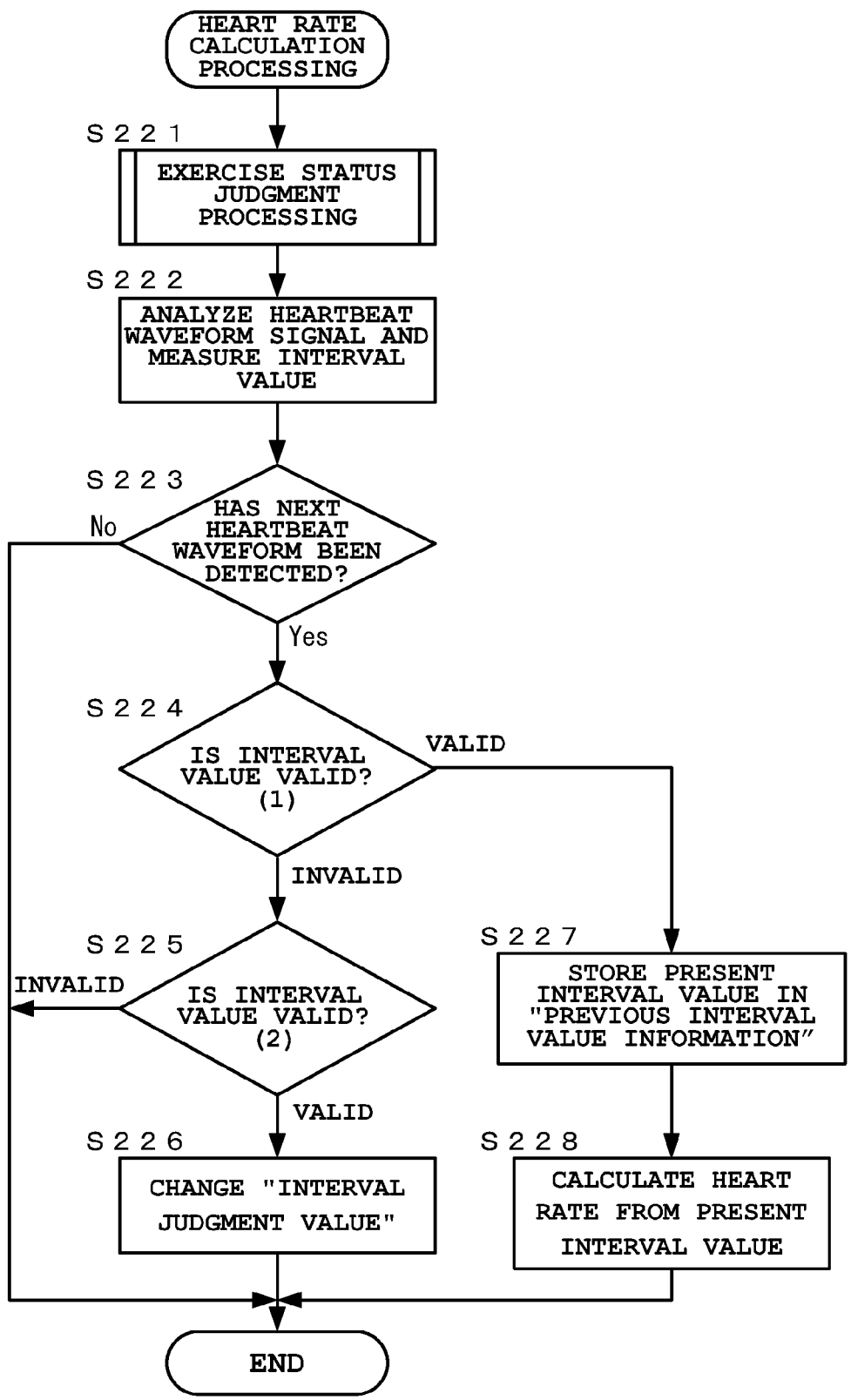
FIG. 8 is a flowchart of heart rate calculation processing applied in the exercise support method according to the first embodiment.

FIG. 8 is a flowchart of the heart rate calculation processing applied in the exercise support method according to the present embodiment. FIG. 9A and FIG. 9B are signal waveform diagrams depicting examples of heartbeat data at the time of walking and running outputted from the heartbeat sensor applied in the exercise support apparatus according to the present embodiment.

Specifically, in the heart rate calculation processing applied in the present embodiment, the CPU 114 first reads out the clock data calculated by the footstep count calculation processing and stored in the "clock information" to perform exercise status judging processing at Step S221, and outputs "exercise status judgment information" reset by the exercise status judgment processing, as depicted in FIG. 8. A specific example of the exercise status judgment processing will be described further below.

Next, at Step S222, the CPU 114 starts an operation of sequentially analyzing waveform signals such as those depicted in FIG. 9A and FIG. 9B which are heartbeat data detected by the heartbeat sensor 111, and increments an interval value. Here, as depicted in FIG. 9A and FIG. 9B, the interval value is found by measuring a time between peak values of a signal level in waveform signals indicating the heartbeat data at the time of walking (FIG. 9A) and running (FIG. 9B) outputted from the heartbeat sensor 111. Since the data sampling rate in the present embodiment is 200 Hz, one count corresponds to 5 ms when the interval value is converted to time.

Next, at Step S223, the CPU 114 judges whether the next heartbeat waveform has been detected by the heartbeat sensor 111. If a heartbeat waveform has not been detected, the CPU 114 ends the heart rate calculation processing. On the other hand, if a heartbeat waveform has been detected, the CPU 114 judges at Step S224 whether the interval value is valid or invalid based on the following properness judgment conditions (1-a) and (1-b) (first condition).

That is, in judgment processing based on the properness judgment condition (1-a) at Step S224, the CPU 114 judges whether the present interval value indicates a normal heart rate. Specifically, for example, the CPU 114 judges whether the present interval value is within a normal heart rate range (a lower-limit value of 54 to an upper-limit value of 600) based on the following conditional expression (11).

Properness Judgment Condition (1-a):

$$54(220\text{BPM}) \leq \text{present interval value} \leq 600(20\text{BPM}) \tag{11}$$

Also, in judgment processing based on the properness judgment condition (1-b) at Step S224, the CPU 114 compares an average value of the last ten interval values during an exercise with the present interval value and, when the present interval value has abruptly changed, the CPU 114 judges the interval value as invalid because the heartbeat waveform has been generated by noise. Specifically, the CPU 114 judges whether the interval value is within a range of valid interval values (a range of 0.8 to 1.2 times of the average interval value, or in other words, a range of ±20% with reference to the average interval value) based on, for example, whether the following conditional expression (12) is satisfied. Here, magnifications of "0.8" (allowable range lower-limit value; first coefficient) and "1.2" (allowable range upper-limit value; second coefficient) or ±20 defining the range of the interval values is a numerical value defining a range where favorable removal of noise obtained as a result of various verifications by the inventor can be achieved.

Properness Judgment Condition (1-b):

$$\text{allowable range lower-limit value}(0.8) \times \text{average value} \\ \text{of the last ten interval values} \leq \text{present interval} \\ \text{value} \leq \text{allowable range upper-limit value}(1.2) \times \\ \text{average value of the last ten interval values} \tag{12}$$

When the present interval value satisfies the conditional expression (12) and is judged as valid at Step S224, the CPU 114 stores the present interval value in previous interval value information and rests the present interval value at Step S227. Next at Step S228, the CPU 114 calculates a heart rate from the present interval value by using, for example, the following equation (13), and ends the heart rate calculation processing.

$$\text{Heart rate} = 60/(\text{average value of the last ten interval} \\ \text{values} \times 0.005) \tag{13}$$

On the other hand, when the present interval value does not satisfy the conditional expression (12) and is judged as invalid at Step S224, the CPU 114 judges at Step S225 whether the interval value is valid or invalid based on the following state judgment conditions (2-a) to (2-d) (a second condition).

That is, in judgment processing based on the state judgment conditions (2-a) and (2-b) at Step S225, the CPU 114 judges a change state of the present interval value. Specifically, the CPU 114 judges whether the present interval value is in an [increase] state based on whether the following conditional expression (21) of the state judgment condition (2-a) is satisfied. Also, the CPU 114 judges whether the present interval value is in a [decrease] state based on whether the following conditional expression (22) of the state judgment condition (2-b) is satisfied. Here, the satisfaction of the expression (21) indicates that the present interval value is gradually decreasing, which corresponds to an increase of the heart rate. This state represents in the specification that the present interval value is in an [increase] state. Similarly, the satisfaction of the expression (22) indicates that the present interval value is gradually increasing, which corresponds to a decrease of the heart rate. This state represents in the specification that the present interval value is in a [decrease] state.

State Judgment Condition (2-a):

$$\text{allowable range lower-limit value}(0.8) \times \text{average value} \\ \text{of the last ten interval values} > \text{present interval} \\ \text{value} \tag{21}$$

State Judgment Condition (2-b):

$$\text{allowable range upper-limit value}(1.2) \times \text{average value} \\ \text{of the last ten interval values} < \text{present interval} \\ \text{value} \tag{22}$$

In judgment processing based on the state judgment conditions (2-c) and (2-d) at Step S225, the CPU 114 makes a comparison with "exercise status judgment information" judged and set by exercise status judgment processing described below according to the change state of "increase" or "decrease" of the present interval value judged in the judgment processing based on the state judgment conditions (2-a) and (2-b), and thereby judges whether the interval value is valid or invalid. Specifically, when the present interval value is judged as being in an [increase] state in the judgment processing based on the state judgment condition (2-a), the CPU 114 judges whether the present interval value is valid or invalid based on the following state judgment condition (2-c).

State Judgment Condition (2-c):

In a case where the state judgment condition (2-a) is satisfied and the present interval value is smaller than the allowable range lower-limit value of the average interval value, the CPU 114 makes a comparison with the "exercise status judgment information", and judges that the present interval value is "valid" when the "exercise status judgment information" indicates walking [UP] or running [UP]. On the other hand, when the "exercise status judgment information" indicates anything other than walking [UP] or running [UP], the CPU 114 judges that the present interval value is "invalid".

When the present interval value is judged as being in a [decrease] state in the judgment processing based on the state judgment condition (2-b), the CPU 114 judges whether the present interval value is valid or invalid based on the following state judgment condition (2-d).

State Judgment Condition (2-d):

In a case where the state judgment condition (2-b) is satisfied and the present interval value is larger than the allowable range upper-limit value of the average interval value, the CPU 114 makes a comparison with the "exercise status judgment information", and judges that the present interval value is "valid" when the "exercise status judgment information" indicates stop, walking [DOWN], or running [DOWN]. On the other hand, when the "exercise status judgment information" indicates anything other than stop, walking [DOWN], or running [DOWN], the CPU 114 judges that the present interval value is "invalid".

When the present interval value is judged as "invalid" at Step S225, the CPU 114 ends the heart rate calculation processing. On the other hand, when the present interval value is judged as "valid", the CPU 114 changes an "interval judgment value" so as to expand the "allowable range lower-limit value" of the "allowable range upper-limit value" at Step S226, and ends the heart rate calculation processing.

Here, specific numerical values in the interval value judgment processing including the above-described Steps S224 to S228 verified by the inventor are described. When the present interval value obtained based on a waveform signal indicating heartbeat data outputted from the heartbeat sensor 111 is 60 (200 BPM), and "0.8" and "1.2" are set as default values in the "allowable range lower-limit value" and the "allowable range upper-limit value" depicted in the management information of Table 2, respectively, the CPU 114 judges the present interval value as valid if the present interval value is within a range represented by the following conditional expression (31) in the judgment processing based on the properness judgment conditions (1-a) and (1-b).

$$48(250BPM) \leq 60 \text{ (present interval value)} \leq 72 \text{ (166BPM)} \quad (31)$$

On the other hand, when the present interval value is clocked as, for example, 75, the present interval value is judged as invalid in the judgment processing based on the properness judgment condition (1-a).

Next, when the present interval value is judged as valid in the judgment processing based on the state judgment conditions (2-a) to (2-d), the magnification of the "allowable range upper-limit value" depicted in the management information of Table 2 is changed from "1.2" to "1.3". Then, at the time of sampling the next heartbeat data by the heartbeat sensor 111, the changed "allowable range upper-limit value" is used. As a result, in the judgment processing based on the properness judgment conditions (1-a) and (1-b), the present interval value is within the range of the following conditional expression (32) and is judged as valid.

$$48(250BPM) \leq 60 \text{ (present interval value)} \leq 78 \text{ (153BPM)} \quad (32)$$

Here, a change amount of the magnification of the "allowable range upper-limit value" is an amount achieved by the number of significant figures being two for a value obtained by multiplying the "allowable range upper-limit value" before change by 1.1. Similarly, the number of significant figures may be two for a value obtained by multiplying the "allowable range upper-limit value" before change by 0.9. If the conditional expression (32) is not satisfied after the magnification of the "allowable range upper-limit value" or the "allowable range lower-limit value" is changed, this case is regarded as a device failure.

(Specific Example of Exercise Status Judgment Processing)

Next, the exercise status judgment processing applied in the heart rate calculation processing is described.

Figure 10:
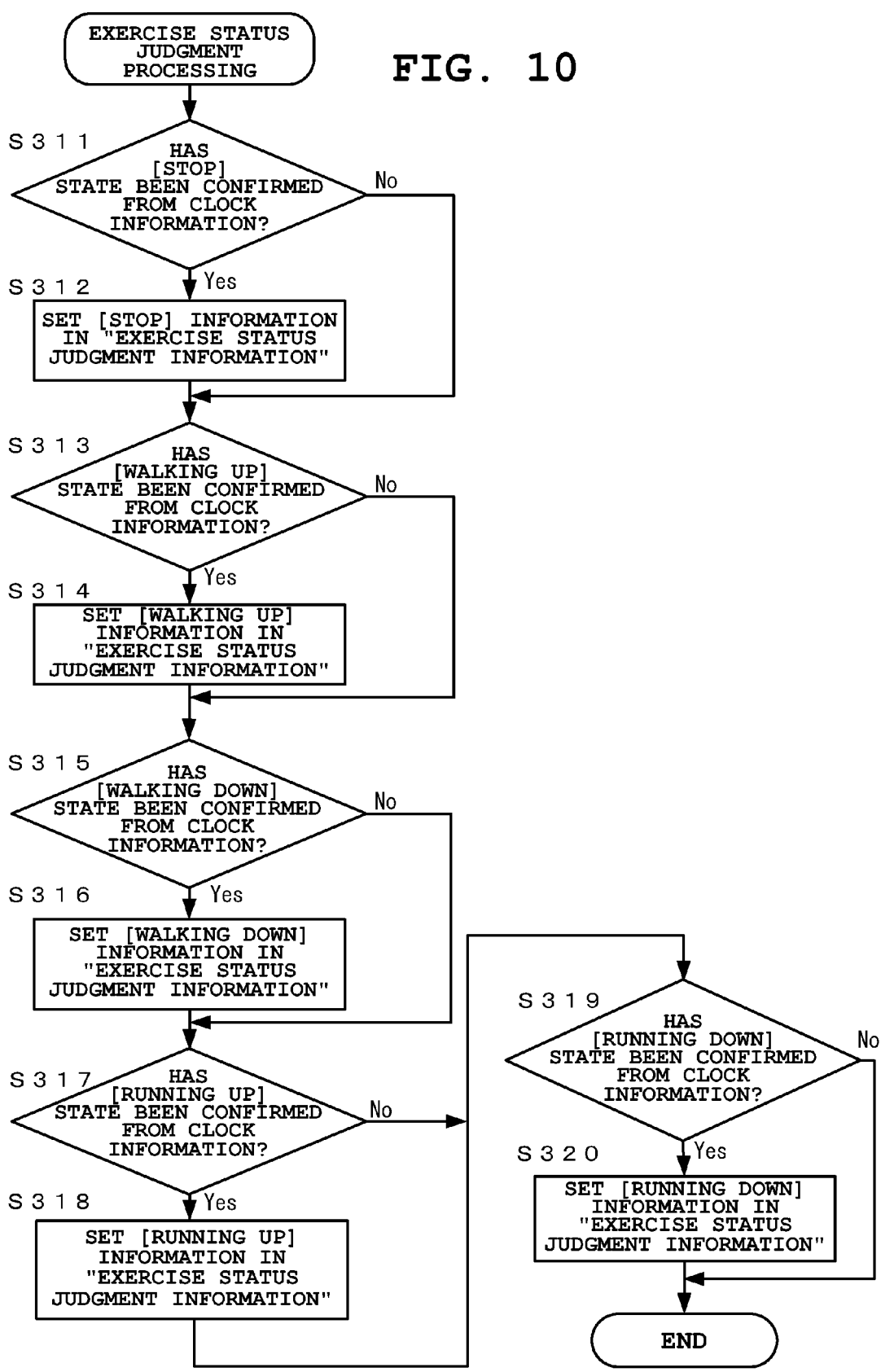
FIG. 10 is a flowchart of exercise status judgment processing applied in the exercise support method according to the first embodiment.

FIG. 10 is a flowchart of the exercise status judgment processing applied in the exercise support method according to the preset embodiment.

In the exercise status judgment processing applied in the exercise support method according to the present embodiment, a processing operation starts by the CPU 114 calling a module of the exercise status judgment processing of the algorithm program.

In the exercise status judgment processing applied in the preset embodiment, at Step S311, the CPU 114 first judges whether the user US is in a [stop] state based on the "clock information" calculated by the footstep count calculation processing, as depicted in FIG. 10. Specifically, the CPU 114 reads out clock data for the last ten seconds from the "clock information" where the clock data calculated by the footstep count calculation processing has been stored, and judges whether these clock data are "0". When all the clock data for ten seconds are "0", the CPU 114 judges that the user US is in a [stop] state and sets [stop] information in the "exercise status judgment information" at Step S312. On the other hand, when any of the clock data for ten seconds is not "0" at Step S311, the CPU 114 judges that the user US is not in a [stop] state, and proceeds to Step S313.

Next, the CPU 114 judges an exercise status based on a change state of the "clock information". Specifically, at Step S313, the CPU 114 reads out clock data for ten seconds from the "clock information" and judges whether an exercise status ten seconds before the present time and a current exercise status are each a walking state or a running state. Here, the CPU 114 judges that the exercise status is a walking state when the footstep count per second is smaller than 2.35 and the exercise status is a running state when the footstep count per second is equal to or larger than 2.35. Then, when the exercise status ten seconds before the present time is a walking state and the current footstep count per second is larger than the footstep count per second ten seconds before the present time, the CPU 114 judges that the user US is in a [walking UP] state (walking up state), and sets [walking UP] information in the "exercise status judgment information" at Step S314. On the other hand, when judged that the user US is not in a [walking UP] state, the CPU 114 proceeds to Step S315.

Next at Step S315, the CPU 114 reads out clock data for ten seconds from the "clock information". When the exercise status ten seconds before the present time and the current exercise status are both walking states and the current footstep count per second is smaller than the footstep count per second ten seconds before the present time, the CPU 114 judges that the user US is in a [walking DOWN] state (walking down state), and sets [walking DOWN] information in the "exercise status judgment information" at Step S316. On the other hand, when judged that the user US is not in a [walking DOWN] state at Step S315, the CPU 114 proceeds to Step S317.

Next at Step S317, the CPU 114 reads out clock data for ten seconds from the "clock information". When the exercise status ten seconds before the present time and the current exercise status are both running states and the current footstep count per second is larger than the footstep count per second ten seconds before the present time, the CPU 114 judges that the user US is in a [running UP] state (running up state), and sets [running UP] information in the "exercise status judgment information" at Step S318. On the other hand, when judged that the user US is not in a [running UP] state at Step S317, the CPU 114 proceeds to Step S319.

Next, at Step S319, the CPU 114 reads out clock data for ten seconds from the "clock information". When the exercise status ten seconds before the present time is a running state and the current footstep count per second is smaller than the footstep count per second ten seconds before the present time, the CPU 114 judges that the user US is in a [running DOWN] state (running down state), and sets [running DOWN] information in the "exercise status judgment information" at Step S320. On the other hand, when judged that the user US is not in a [running DOWN] state at Step S319, the CPU 114 ends the processing.

By this series of exercise status judgment processing, a time between peak values of the waveform signal level judged as a "footstep count" in the waveform signals indicating acceleration data from the acceleration sensor 112 is measured as depicted in FIG. 7A and FIG. 78. As a result, the exercise status of whether the user US is stopping, walking, or running is judged. Then, the "exercise status judgment information" where the exercise status of the user US has been set is applied to a comparison with the change state of the present interval value in the comparison processing (Step S225) performed in the heart rate calculation processing described above so as to judge whether the interval value is valid or invalid, whereby a heart rate is calculated based on the interval value judged as valid. That is, in the waveform signals indicating heartbeat data from the heartbeat sensor 111 depicted in FIG. 9A and FIG. 9B, interval values 1c to 5c obtained by measurement by erroneously detecting peak values of the signal level of noise signal due to the exercise (body movement) of the user US are judged as invalid. On the other hand, interval values 1a to 2a and 1b to 3b obtained by measurement by detecting peak values of the signal level of a correct heartbeat signal are judged as valid, and a heart rate (the number of heartbeats per minute) is calculated based on the interval values 1a to 2a and 1b to 3b judged as valid.

Then, the exercise information including the heart rate and the footstep count calculated by the above-described exercise support apparatus and exercise support method and the exercise status judgment information is transmitted via the communication function section 118 of the sensor device 100 to the interface device 200 by using a predetermined communication method. The interface device 200 associates the received pieces of exercise information with each other and stores the result information in a predetermined storage area of the exercise information storage memory 214.

Next, in the operation of providing the exercise information and the support information to the user US, the CPU 213 of the interface device 200 reads out the exercise information stored in the exercise information storage memory 214, and causes the read information to be displayed on the display section 211 in a predetermined display format by using numerical value information and character information as depicted in FIG. 1C. Here, the exercise information to be displayed on the display section 211 may be the current or immediately-previous footstep count, heart rate, running time, run distance, etc., of the user US during a exercise, or previous exercise information may be displayed thereon.

Also, a configuration may be adopted in which the CPU 213 of the interface device 200 analyzes the exercise information (that is, the footstep count, the heart rate, the exercise status, etc.) read out from the exercise information storage memory 214 by using an algorithm, judges whether the footstep count, the heart rate, and the exercise status are normal, and displays support information based on the judgment result on the display section 211. Examples of the method of providing the support information in this case include a method of highlighting numerical value information regarding an item for which an advice is particularly given, a method of displaying a specific message (character information) such as "your heart rate is increasing" or "please decrease your pace", and a method of changing a display color of the entire or part of the area of the display section 211 or changing a light-emitting state for blink display. These methods may be applied singly or in any combination. Furthermore, in addition to or in place of display of these exercise information and support information, the interface device 200 may include an acoustic section to provide the above-described exercise information and support information by a specific sound pattern or voice or may include a vibrating section to provide the above-described exercise information and support information by a specific vibration.

As described above, in the present embodiment, an increase or decrease of the heart rate is grasped based on the exercise status of the user US, and noise components included in the heartbeat data can be favorably removed. As a result, a change (decrease) of the heart rate can be reliably detected and measured irrespective of the exercise status (in particular, after the exercise is calmed down). Therefore, the user US can correctly and accurately grasp the exercise information including the footstep count and the heart rate via the interface device 200 at the time of or after an exercise, and thereby can use the exercise information to help healthcare and improve a record in a competition or training.

In the above-described embodiment, as the interface device 200 for providing exercise information and support information to the user US, a dedicated reception terminal of a wristwatch type or a wristband type including a display section, an acoustic section, etc., has been described. However, the present invention is not limited thereto, and an interface device having another structure may be adopted as long as the device is mounted at a position where the exercise information and the support information provided to the user US can be easily recognized. In addition, the device may be mounted on another part of the body. That is, as an interface device to be applied in the present invention, for example, a general-purpose electronic device such as a wristwatch, a portable telephone, or a smartphone may be adopted and mounted on a wrist, an upper arm, or the like, in addition to a dedicated reception terminal. Alternatively, an eyeglasses-type display device having a function of a display section (so-called display glasses) or a voice device having a function of an acoustic device (for example, a media player) may be adopted.

<Second Embodiment>

Next, a second embodiment of the exercise support apparatus in which the exercise information detecting apparatus according to the present invention has been applied is described. Here, the second embodiment is described with reference to the structure (FIG. 1A to 1C, FIG. 2 and FIG. 3) and method (FIG. 4 to FIG. 10) described in the first embodiment.

In the first embodiment described above, in the sensor device 100 mounted on the chest part of the user US, sensor data obtained from the heartbeat sensor 111 and the acceleration sensor 112 is processed to calculate exercise information including a footstep count and a heart rate, and this information is provided to the user US by being transmitted to the interface device 200 mounted on a wrist. In the second embodiment, in the sensor device 100, sensor data obtained from the heartbeat sensor 111 and the acceleration sensor 112 is transmitted to the interface device 200, and the interface device 200 processes the sensor data to calculate exercise information including a footstep count and a heart rate, and provides the calculated exercise information to the user US.

As with the structure of the first embodiment (refer to FIG. 1A to 1C, FIG. 2 and FIG. 3), the exercise support apparatus according to the second embodiment includes the sensor device 100 and the interface device 200. In the sensor device 100 according to the present embodiment, the flash memory 116 in the specific structure described in the first embodiment (refer to FIG. 2) has stored therein only a control program for performing a predetermined operation in each component such as a sensing operation in the heartbeat sensor 111 and the acceleration sensor 112 and a data transmitting operation in the communication function section 118. Also, the work memory 117 temporarily stores only data that are used or generated in executing the control program.

The CPU 114 performs processing by following the control program stored in the flash memory 116, and thereby controls an operation in each component such as a sensing operation in the heartbeat sensor 111 and the acceleration sensor 112 and a data transmitting operation in the communication function section 118. The communication function section 118 functions as an interface when sensor data obtained by the heartbeat sensor 111 and the acceleration sensor 112 is transmitted to the interface device 200.

That is, in the present embodiment, the sensor device 100 has only a function for storing sensor data detected by the heartbeat sensor 111 and the acceleration sensor 112 in the sensor data storage memory 115 and transmitting the sensor data to the interface device 200 via the communication function section 118. Here, In a case where the sensor data storage memory 115 is a removable storage medium such as a memory card and, by the removable storage medium being removed from the sensor device 100, stored sensor data can be transferred to another device without an intervention of the communication function section 118, the sensor device 100 is not required to include the communication function section 118. In this case, the sensor device 100 functions as a data logger.

On the other hand, in the interface device 200 according to the present embodiment, the flash memory 215 in the specific structure described in the first embodiment (refer to FIG. 3) has stored therein a control program for performing a predetermined operation in each component, such as an operation of displaying exercise information and support information on the display section 211 and a data transmitting operation in the communication function section 217. Also, the flash memory 215 has stored therein an algorithm program for processing sensor data transmitted from the sensor device 100 and outputting exercise information such as a footstep count, a heart rate, and an exercise status of the user US. Note that the flash memory 215 may have stored therein an algorithm program for judging whether the exercise status of the user US is good based on exercise information, and outputting support information based on the judgment result. The work memory 216 temporarily stores various data that are used or generated when the control program and the algorithm program are executed.

By following the algorithm program stored in the flash memory 215, the CPU 213 performs, inside the CPU 213, an operation of processing sensor data transmitted from the sensor device 100 and outputting a footstep count, a heart rate, and a exercise status. Also, by following the control program, the CPU 213 controls an operation in each component such as an operation of displaying exercise information and support information on the display section 211 and a data transmitting operation in the communication function section 217. The communication function section 217 functions as an interface when at least sensor data is transmitted to the sensor device 100 by a wireless or wired communication method.

That is, in the present embodiment, the interface device 200 has a function for storing sensor data transmitted from the sensor device 100 in the exercise information storage memory 214, processing the sensor data to output a footstep count, a heart rate, and an exercise status, and providing these data to the user US via the display section 211.

In the present embodiment as well, an increase or decrease of the heart rate at the time of an exercise can be grasped and noise included in the heartbeat data can be favorably removed, as in the case of the first embodiment described above. As a result, a change of the heart rate can be accurately detected and measured irrespective of the exercise status. Therefore, the user US can correctly and adequately grasp the exercise information including the footstep count and the heart rate via the interface device.

Also, in the present embodiment, the processing of sensor data described in the first embodiment can be performed by the interface device 200. Therefore, in comparison with the case described in the first embodiment, the processing load on the sensor device 100 can be reduced, whereby the size and weight of the sensor device 100 can be reduced and the life of the operating power supply can be extended.

<Modification Examples>

Next, modification examples of the exercise support apparatus according to the present embodiment are described.

Figure 11:
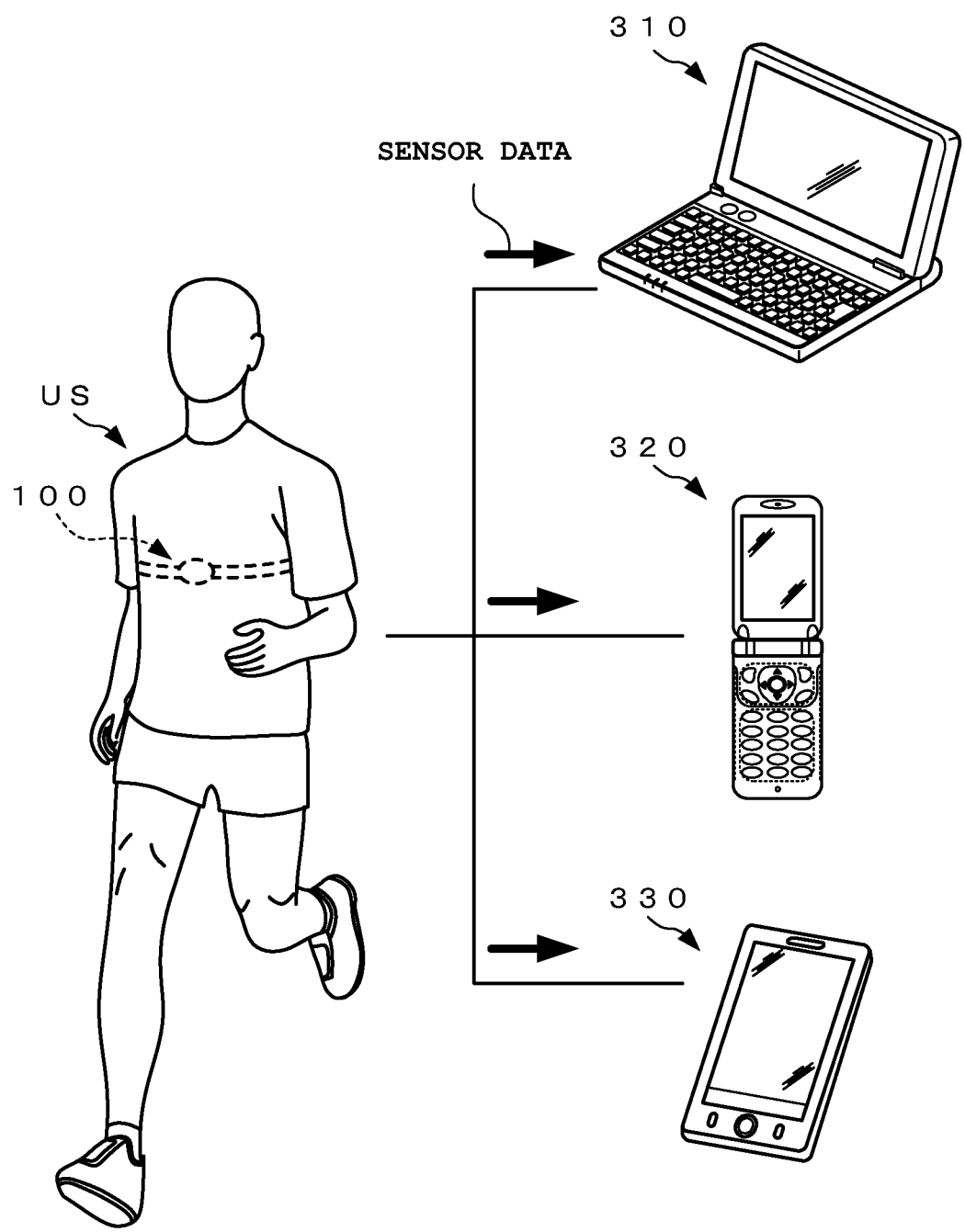
FIG. 11 is a schematic structural diagram of a first modification example of an exercise support apparatus according to a second embodiment.
Figure 12:
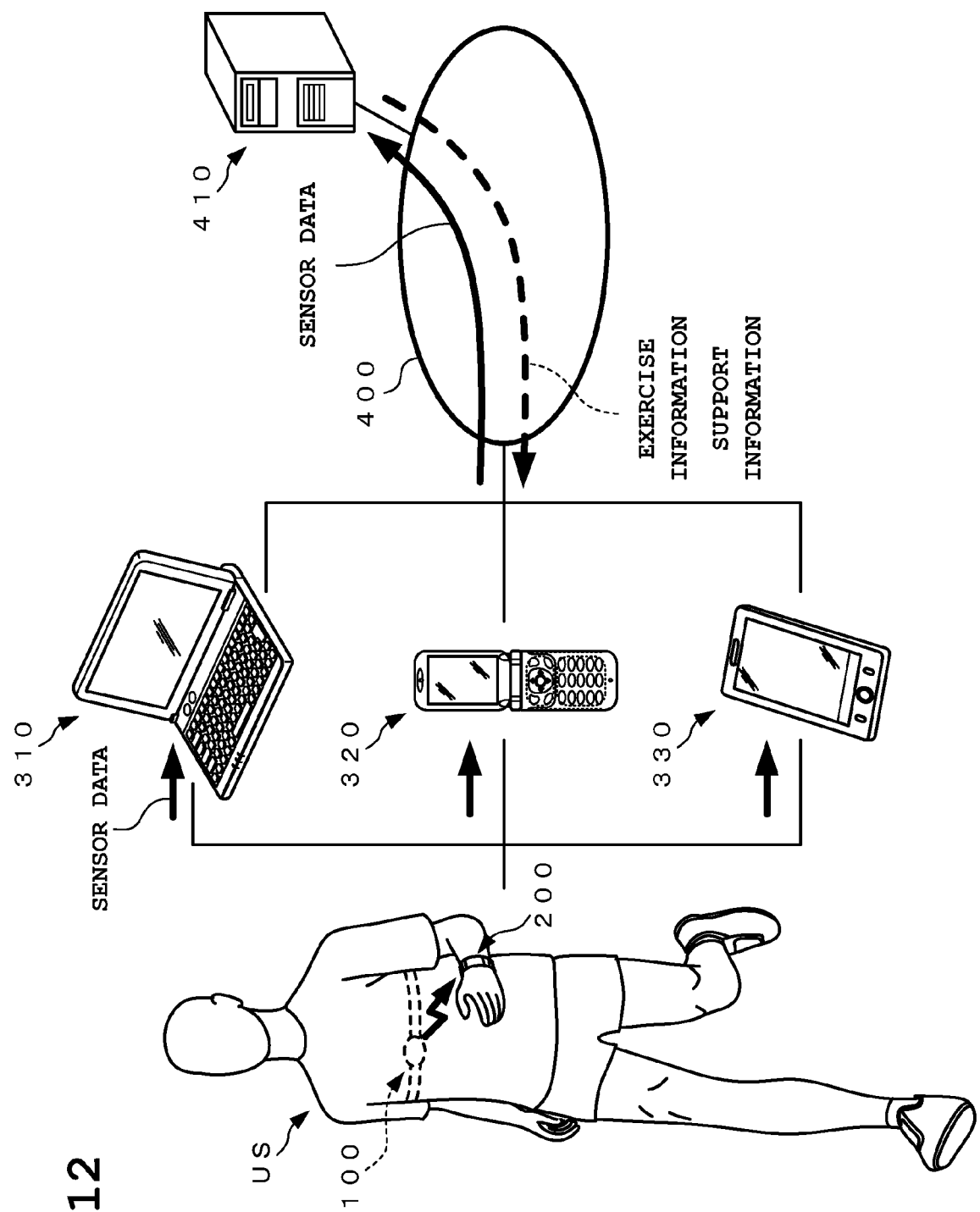
FIG. 12 is a schematic structural diagram of a second modification example of the exercise support apparatus according to the second embodiment.

FIG. 11 and FIG. 12 are schematic structural diagrams of a modification example of the exercise support apparatus according to the second embodiment. Here, components similar to those of the above-described first embodiment are provided with the same reference numerals, and descriptions therefor are simplified or omitted.

In the present embodiment as well, the interface device is not limited to a reception terminal of a wristwatch type or a wristband type, as with the above-described first embodiment. For example, various electronic devices such as a personal computer 310, a portable telephone 320, and a smartphone 330 may be applied, as depicted in FIG. 11. If necessary, in addition to these electronic devices, a server 410 on a network 400 or the like may be applied in combination, as depicted in FIG. 12. Here, in these electronic devices such as the personal computer 310, the portable telephone 320, and the smartphone 330, and the server 410 on the network 400 applied as interface devices, the control program and the algorithm program for performing the exercise support method described in each of the above-described embodiments are incorporated. Also, the transmission of sensor data from the sensor device 100 to these electronic devices may be performed by a wireless or wired communication method or via a removable storage medium such as a memory card. Exercise information and support information including a footstep count and a heart rate obtained and outputted by processing sensor data in the electronic devices are provided to the user US via a display device provided on each of the electronic devices. Also, exercise information and support information including a footstep count and a heart rate obtained and outputted by processing sensor data by the server 410 on the network 400 are transmitted to an arbitrary electronic device via the network 400 and provided to the user US via the display device provided on the electronic device.

In the structures of these modification examples as well, sensor data can be processed by an arbitrary electronic device or server, as with the above-described second embodiment. Therefore, in comparison with the case described in the first embodiment, the processing load on the sensor device 100 can be reduced, whereby the size and weight of the sensor device 100 can be reduced and the life of the operating power supply can be extended.

While the present invention has been described with reference to the preferred embodiments, it is intended that the invention be not limited by any of the details of the description therein but includes all the embodiments which fall within the scope of the appended claims.

What is claimed is:

1. An exercise information detecting apparatus comprising:
a processor; and
a memory storing instructions that, when executed by the processor, control the processor to:
acquire heartbeat data of a target subject detected by a heartbeat sensor while the target subject moves;
acquire acceleration data detected by an acceleration sensor while the target subject moves;
obtain an exercise status of the target subject and judge a change of the exercise status based on the acceleration data; and
based on the change of the exercise status of the target subject, determine whether a first interval value between a certain peak and a previous peak of the certain peak, from among a plurality of peaks included in a waveform signal of the heartbeat data, is valid or invalid and, when the first interval value is determined to be invalid, then determine whether a second interval value between the previous peak and a subsequent peak of the certain peak is valid or invalid, wherein:
the instructions further control the processor to determine that a certain interval value is valid when a first condition is satisfied, the first condition being a condition that the certain interval value is equal to or larger than a lower-limit value and equal to or smaller than an upper-limit value, and that the certain interval value is equal to or larger than a value obtained by multiplying an average value of a plurality of immediately-previous interval values by a first coefficient and equal to or smaller than a value obtained by multiplying the average value by a second coefficient,
the instructions further control the processor to obtain a footstep count per unit time based on more than one peak from among a plurality of peaks included in a waveform signal of the acceleration data, and to determine the change of the exercise status based on a result of a comparison between a current footstep count per unit time and a footstep count per unit time in a certain past time period, and
the instructions further control the processor to determine that the certain interval value is valid when the first condition is not satisfied and a second condition is satisfied, and to determine that the certain interval value is invalid when neither of the first condition and the second condition is satisfied, the second condition being one of a condition that the certain interval value is larger than the upper-limit value and the footstep count per unit time is increasing, and a condition that the certain interval value is smaller than the lower-limit value and the footstep count per unit time is decreasing.

2. The exercise information detecting apparatus according to claim 1, wherein the instructions further control the processor to obtain a heart rate per unit time by using at least one interval value determined to be valid.

3. The exercise information detecting apparatus according to claim 1, wherein the instructions further control the processor to:
revise the first coefficient to a larger value when the second condition that the certain interval value is larger than the upper-limit value and the footstep count per unit time is increasing is satisfied, and
revise the second coefficient to a smaller value when the second condition that the certain interval value is smaller than the lower-limit value and the footstep count per unit time is decreasing is satisfied.

4. The exercise information detecting apparatus according to claim 3, wherein the instructions further control the processor to determine that the exercise status of the target subject is a walking state when the footstep count per unit time is smaller than a certain value, and that the exercise status of the target subject is a running state when the footstep count per unit time is equal to or larger than the certain value.

5. The exercise information detecting apparatus according to claim 4, wherein the instructions further control the processor to:
determine that the exercise status of the target subject is a first walking state, when judging that the exercise status of the target subject in the certain past time period is the walking state and that the current footstep count per unit time is larger than the footstep count per unit time in the certain past time period;
determine that the exercise status of the target subject is a second walking state, when judging that the exercise status of the target subject in the certain past time period and a current exercise status of the target subject are both the walking state and that the current footstep count per unit time is smaller than the footstep count per unit time in the certain past time period;

determine that the exercise status of the target subject is a first running state, when judging that the exercise status of the target subject in the certain past time period and the current exercise status of the target subject are both the running state and that the current footstep count per unit time is larger than the footstep count per unit time in the certain past time period; and determine that the exercise status of the target subject is a second running state, when judging that the exercise status of the target subject in the certain past time period is the running state and that the current footstep count per unit time is smaller than the footstep count per unit time in the certain past time period.

6. The exercise information detecting apparatus according to claim 1, further comprising:
at least one of the heartbeat sensor that detects the heartbeat data and the acceleration sensor that detects the acceleration data.

7. An exercise information detecting method comprising:
acquiring heartbeat data of a target subject detected by a heartbeat sensor while the target subject moves;
acquiring acceleration data detected by an acceleration sensor while the target subject moves;
obtaining an exercise status of the target subject and judging a change of the exercise status based on the acceleration data; and
based on the change of the exercise status of the target subject, determining whether a first interval value between a certain peak and a previous peak of the certain peak, from among a plurality of peaks included in a waveform signal of the heartbeat data, is valid or invalid and, when the first interval value is determined to be invalid, then determining whether a second interval value between the previous peak and a subsequent peak of the certain peak is valid or invalid,
wherein:
the determining determines that a certain interval value is valid when a first condition is satisfied, the first condition being a condition that the certain interval value is equal to or larger than a lower-limit value and equal to or smaller than an upper-limit value, and that the certain interval value is equal to or larger than a value obtained by multiplying an average value of a plurality of immediately-previous interval values by a first coefficient and equal to or smaller than a value obtained by multiplying the average value by a second coefficient,
the obtaining obtains a footstep count per unit time based on more than one peak from among a plurality of peaks included in a waveform signal of the acceleration data, and determines the change of the exercise status based on a result of a comparison between a current footstep count per unit time and a footstep count per unit time in a certain past time period, and
the determining determines that the certain interval value is valid when the first condition is not satisfied and a second condition is satisfied, and determines that the certain interval value is invalid when neither of the first condition and the second condition is satisfied, the second condition being one of a condition that the certain interval value is larger than the upper-limit value and the footstep count per unit time is increasing, and a condition that the certain interval value is smaller than the lower-limit value and the footstep count per unit time is decreasing.

8. A non-transitory computer-readable storage medium having stored thereon an exercise information detection program, the program being executable by a computer to control the computer to perform functions comprising:
acquiring heartbeat data of a target subject detected by a heartbeat sensor while the target subject moves;
acquiring acceleration data detected by an acceleration sensor while the target subject moves;
obtaining an exercise status of the target subject and judging a change of the exercise status based on the acceleration data; and
based on the change of the exercise status of the target subject, determining whether a first interval value between a certain peak and a previous peak of the certain peak, from among a plurality of peaks included in a waveform signal of the heartbeat data, is valid or invalid and, when the first interval value is determined to be invalid, then determining whether a second interval value between the previous peak and a subsequent peak of the certain peak is valid or invalid,
wherein:
the determining determines that a certain interval value is valid when a first condition is satisfied, the first condition being a condition that the certain interval value is equal to or larger than a lower-limit value and equal to or smaller than an upper-limit value, and that the certain interval value is equal to or larger than a value obtained by multiplying an average value of a plurality of immediately-previous interval values by a first coefficient and equal to or smaller than a value obtained by multiplying the average value by a second coefficient,
the obtaining obtains a footstep count per unit time based on more than one peak from among a plurality of peaks included in a waveform signal of the acceleration data, and determines the change of the exercise status based on a result of a comparison between a current footstep count per unit time and a footstep count per unit time in a certain past time period, and
the determining determines that the certain interval value is valid when the first condition is not satisfied and a second condition is satisfied, and determines that the certain interval value is invalid when neither of the first condition and the second condition is satisfied, the second condition being one of a condition that the certain interval value is larger than the upper-limit value and the footstep count per unit time is increasing, and a condition that the certain interval value is smaller than the lower-limit value and the footstep count per unit time is decreasing.

9. An exercise information detecting system comprising:
a heartbeat sensor that detects heartbeat data of a target subject while the target subject moves;
an acceleration sensor that detects acceleration data while the target subject moves;
a processor; and
a memory storing instructions that, when executed by the processor, control the processor to:
acquire the heartbeat data of the target subject detected by the heartbeat sensor;
acquire the acceleration data detected by the acceleration sensor;
obtain an exercise status of the target subject and judge a change of the exercise status based on the acceleration data; and
based on the change of the exercise status of the target subject, determine whether a first interval value between a certain peak and a previous peak of the certain peak, from among a plurality of peaks included in a waveform signal of the heartbeat data, is valid or invalid and, when the first interval value is determined to be invalid, then determine whether a second interval value between the previous peak and a subsequent peak of the certain peak is valid or invalid, wherein:

the instructions further control the processor to determine that a certain interval value is valid when a first condition is satisfied, the first condition being a condition that the certain interval value is equal to or larger than a lower-limit value and equal to or smaller than an upper-limit value, and that the certain interval value is equal to or larger than a value obtained by multiplying an average value of a plurality of immediately-previous interval values by a first coefficient and equal to or smaller than a value obtained by multiplying the average value by a second coefficient, the instructions further control the processor to obtain a footstep count per unit time based on more than one peak from among a plurality of peaks included in a waveform signal of the acceleration data, and to determine the change of the exercise status based on a result of a comparison between a current footstep count per unit time and a footstep count per unit time in a certain past time period, and the instructions further control the processor to determine that the certain interval value is valid when the first condition is not satisfied and a second condition is satisfied, and to determine that the certain interval value is invalid when neither of the first condition and the second condition is satisfied, the second condition being one of a condition that the certain interval value is larger than the upper-limit value and the footstep count per unit time is increasing, and a condition that the certain interval value is smaller than the lower-limit value and the footstep count per unit time is decreasing.

\* \* \* \* \*